(12) United States Patent
Griffith

(10) Patent No.: US 12,290,686 B2
(45) Date of Patent: May 6, 2025

(54) SYSTEMS AND DEVICES FOR EQUALIZING TELEMETRY SIGNALS TRANSMITTED BY WAY OF A TRANSCUTANEOUS NARROWBAND INDUCTIVE LINK

(71) Applicant: Advanced Bionics AG, Staefa (CH)

(72) Inventor: Glen A. Griffith, Newbury Park, CA (US)

(73) Assignee: Advanced Bionics AG, Staefa (CH)

( * ) Notice: Subject to any disclaimer, the term of this patent is extended or adjusted under 35 U.S.C. 154(b) by 444 days.

(21) Appl. No.: 17/641,694

(22) PCT Filed: Sep. 17, 2019

(86) PCT No.: PCT/US2019/051426
§ 371 (c)(1),
(2) Date: Mar. 9, 2022

(87) PCT Pub. No.: WO2021/054940
PCT Pub. Date: Mar. 25, 2021

(65) Prior Publication Data
US 2022/0296896 A1 Sep. 22, 2022

(51) Int. Cl.
*A61N 1/37* (2006.01)
*A61N 1/05* (2006.01)
*A61N 1/36* (2006.01)

(52) U.S. Cl.
CPC ....... *A61N 1/36038* (2017.08); *A61N 1/0541* (2013.01); *H04R 2225/67* (2013.01)

(58) Field of Classification Search
CPC ........... A61N 1/37211–37229; A61N 1/36038; A61N 1/0541
See application file for complete search history.

(56) References Cited

U.S. PATENT DOCUMENTS 5,891,184 A * 4/1999 Lee .................... A61N 1/37211
607/31
5,991,664 A 11/1999 Seligman
(Continued)

FOREIGN PATENT DOCUMENTS

| EP | 2376185 | 10/2011 |
|---|---|---|
| WO | 2010056768 | 5/2010 |

OTHER PUBLICATIONS

"International Search Report and Written Opinion received in International Application No. PCT/US2019/034596, dated Oct. 24, 2019.".

(Continued)

*Primary Examiner* — Eric D. Bertram
(74) *Attorney, Agent, or Firm* — ALG Intellectual Property, LLC

(57) ABSTRACT

An exemplary cochlear implant system includes a sound processor, a cochlear implant, and equalization circuitry integrated within the sound processor and/or the cochlear implant. The sound processor operates externally to a recipient and is associated with a sound processor coil. The cochlear implant includes a cochlear implant coil larger than the sound processor coil and that is configured to form a transcutaneous narrowband inductive link with the sound processor coil when the cochlear implant is implanted within the recipient. By way of the transcutaneous narrowband inductive link, the cochlear implant receives a forward telemetry signal incorporating power and forward telemetry data. The equalization circuitry facilitates recovery, by the cochlear implant, of the forward telemetry data from the forward telemetry signal by compensating for distortion introduced onto the forward telemetry signal as a result of bandwidth limitations imposed by the transcutaneous nar- (Continued)

rowband inductive link. Corresponding systems and devices are also disclosed.

8 Claims, 10 Drawing Sheets

(56) References Cited

U.S. PATENT DOCUMENTS

| | | | | |
|---|---|---|---|---|
| 6,223,083 | B1* | 4/2001 | Rosar | A61N 1/37211 |
| | | | | 128/903 |
| 6,301,504 | B1* | 10/2001 | Silvian | A61N 1/37223 |
| | | | | 607/60 |
| 10,646,164 | B1 | 5/2020 | Perryman et al. | |
| 11,251,660 | B2* | 2/2022 | Karunasiri | H02J 50/20 |
| 11,973,354 | B2* | 4/2024 | Karunasiri | A61N 1/37252 |
| 2005/0251225 | A1 | 11/2005 | Faltys | |
| 2006/0190059 | A1* | 8/2006 | Griffith | A61N 1/36038 |
| | | | | 607/57 |
| 2011/0009924 | A1 | 1/2011 | Meskens | |
| 2011/0150255 | A1 | 6/2011 | Solum | |
| 2011/0208329 | A1 | 8/2011 | Castor-Perry | |
| 2012/0213394 | A1* | 8/2012 | Fort | H04R 25/554 |
| | | | | 381/315 |
| 2014/0240604 | A1 | 8/2014 | Toba et al. | |
| 2015/0073500 | A1* | 3/2015 | Kothandaraman | |
| | | | | A61N 1/37252 |
| | | | | 607/59 |
| 2015/0352359 | A1 | 12/2015 | Fredelake | |
| 2016/0042205 | A1* | 2/2016 | Paris | G06K 7/10148 |
| | | | | 604/891.1 |
| 2016/0375243 | A1 | 12/2016 | Roehrlein et al. | |
| 2017/0028199 | A1 | 2/2017 | Roehrlein et al. | |
| 2017/0189694 | A1 | 7/2017 | Palmer | |
| 2017/0244495 | A1 | 8/2017 | Ouzounov | |
| 2017/0246462 | A1* | 8/2017 | Meskens | H02J 7/00034 |
| 2018/0050198 | A1 | 2/2018 | Mazanec | |
| 2019/0372405 | A1 | 12/2019 | Karunasiri | |
| 2021/0083529 | A1* | 3/2021 | Karunasiri | G06F 1/04 |
| 2021/0337326 | A1* | 10/2021 | Brehm | A61N 1/37229 |
| 2022/0123603 | A1* | 4/2022 | Karunasiri | H04R 1/1025 |

OTHER PUBLICATIONS

"International Search Report and Written Opinion received in International Application No. PCT/US2019/051426, dated Jun. 18, 2020.".

Garcerán-Harnández, et al., "Cochlear implant: Transcutaneous transmission link with OFDM", Jun. 10, 2013, Natural and Artificial Models in Computation and Biology, Springer Berlin Heidelberg, Berlin. pp. 358-367, XP047030847. ISBN: 978-3-642-38636-7; pp. 358-363; figure 1.

Asgarian, et al., "A Low-Power Noncoherent BPSK Demodulator and Clock Recovery Circuit for High-Data-Rate Biomedical Applications", 31st Annual Conference of the IEEE EMBS, Sep. 3, 2009.

* cited by examiner

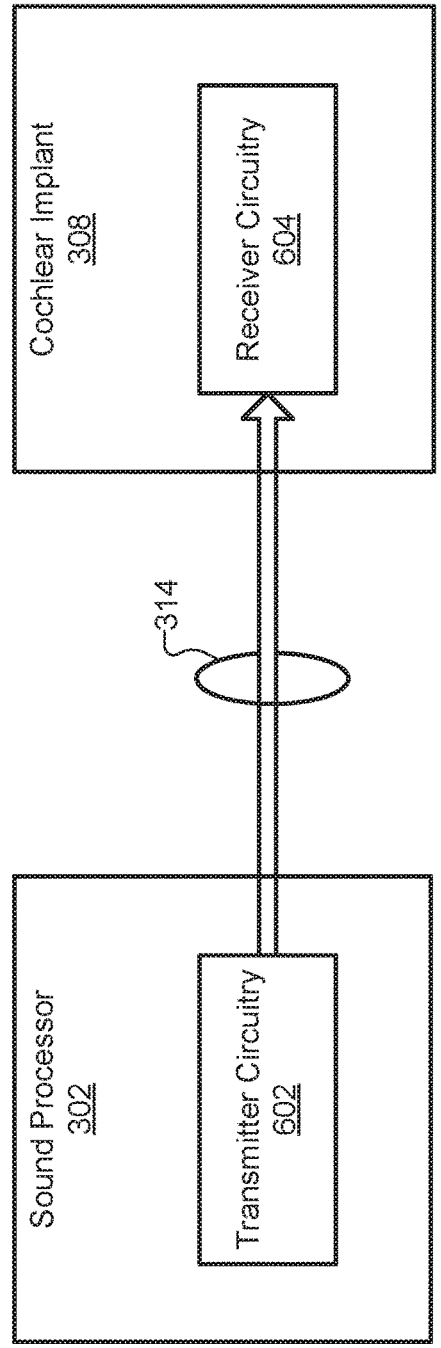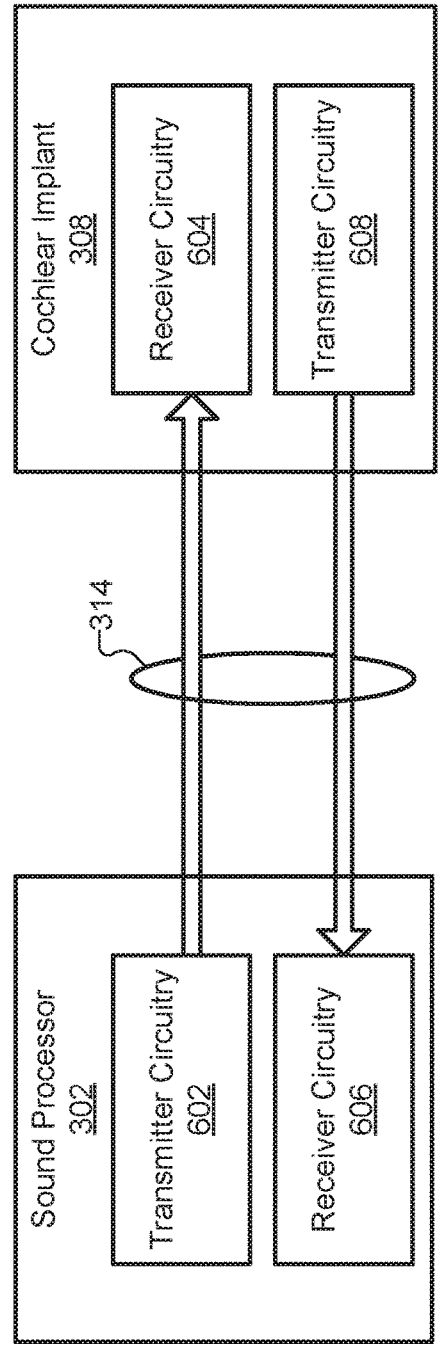

SYSTEMS AND DEVICES FOR EQUALIZING TELEMETRY SIGNALS TRANSMITTED BY WAY OF A TRANSCUTANEOUS NARROWBAND INDUCTIVE LINK

BACKGROUND INFORMATION

Various types of implanted medical systems and devices utilize power and data that is transmitted by way of transcutaneous inductive links. For instance, cochlear implant systems, heart pacemakers, deep brain simulators, urinary incontinence devices, and various other such medical systems and devices may make use of such transcutaneous inductive links. While most of these devices do not require high rates of data to be transferred from external to internal components, cochlear implant systems typically do require continuous data transfer at relatively large transfer rates for proper operation. To maximize the effectiveness and efficiency of such power and data transfer, an implanted coil may typically be inductively coupled with an external coil that is housed in a headpiece magnetically attached to the head of a cochlear implant recipient and communicatively coupled (e.g., by way of a cable or the like) to a sound processor of the cochlear implant system.

While this type of implementation works well for cochlear implant systems, there remains room for improvement with regard to how external sound processors and implanted cochlear implants are configured to transfer power and data effectively and efficiently. For example, it might be desirable (e.g., for the comfort, convenience, and appearance of the recipient, etc.) for a sound processor and a cochlear implant to communicate directly, thereby eliminating the need for a separate headpiece and associated cable.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 6A illustrates an exemplary half-duplex transcutaneous inductive link according to principles described herein.

FIG. 6B illustrates an exemplary full-duplex transcutaneous inductive link according to principles described herein.

DETAILED DESCRIPTION

Figure 1:
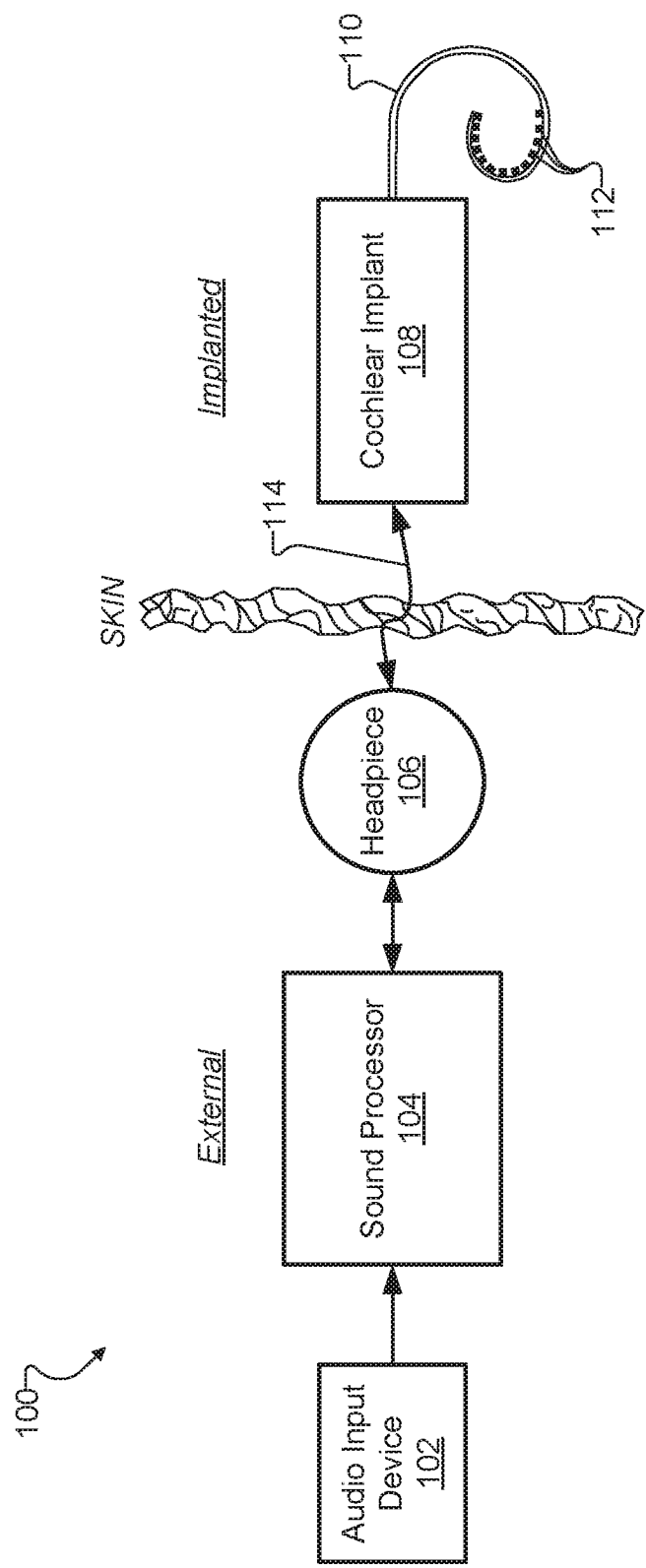
FIG. 1 illustrates an exemplary cochlear implant system according to principles described herein.

Systems and devices for equalizing telemetry signals transmitted by way of a transcutaneous narrowband inductive link are described herein. For example, as will be described and illustrated below, when equalization circuitry equalizes forward and/or backward telemetry signals before or after (or both before and after) transmission by way of a transcutaneous inductive link, the signals may reliably and efficiently carry telemetry data at a relatively high data rate (e.g., a rate used by a medical device such as a cochlear implant system).

In some examples, coils used to transcutaneously transfer power and data for a cochlear implant system may be configured in various ways that provide benefits to a recipient of the cochlear implant system, and yet also create various challenges. For instance, the coils may be disparately sized (e.g., such that an implanted coil is significantly larger than an external coil, etc.) to reduce spacing and/or alignment requirements of the coils for efficient power transfer and, in some cases, even making it possible for power to be efficiently transferred without a separate headpiece and cable. However, configuring the coils in these ways may introduce challenges such as narrowing a bandwidth of the inductive link over which telemetry data is transferred, thereby causing significant distortion to be introduced onto signals carried by the relatively narrowband link. Systems and devices described herein for equalizing telemetry signals may help reduce, eliminate, correct, and/or otherwise compensate for such distortion so that data may be reliably carried over transcutaneous narrowband inductive links at data rates sufficient for proper functionality of cochlear implant systems.

As will be described in more detail below, an exemplary cochlear implant system for equalizing telemetry signals transmitted by way of a transcutaneous narrowband inductive link may include a sound processor, a cochlear implant, and equalization circuitry integrated within at least one of the sound processor and the cochlear implant (e.g., integrated entirely within the sound processor, entirely within the cochlear implant, or distributed across both the sound processor and the cochlear implant).

The sound processor may be configured to operate externally to a recipient of the cochlear implant system, and may be associated with a sound processor coil. For example, the sound processor coil may be integrated into the sound processor (e.g., physically housed within a single housing of the sound processor, rather than, for instance, in a housing of a headpiece separate from the rest of the sound processor).

The cochlear implant may include a cochlear implant coil that is configured to form a transcutaneous narrowband inductive link with the sound processor coil when the cochlear implant is implanted within the recipient. In some examples, the cochlear implant coil may have a size (e.g., a diameter, an area, etc.) that is larger than a size of the sound processor coil. As such, the cochlear implant coil may enable the cochlear implant to receive (e.g., from the sound processor by way of the transcutaneous narrowband inductive link) a forward telemetry signal that incorporates both 1) power for powering operations of the cochlear implant, and 2) forward telemetry data for directing the operations of the cochlear implant.

Whether integrated within the sound processor, the cochlear implant, or both, the equalization circuitry may be configured to facilitate recovery, by the cochlear implant, of the forward telemetry data from the forward telemetry signal. For example, the equalization circuitry may facilitate recovery of the forward telemetry data by compensating for distortion introduced onto the forward telemetry signal as a result of bandwidth limitations imposed by the transcutaneous narrowband inductive link.

In addition to system implementations such as the cochlear implant system described above, certain systems and devices described herein for equalizing telemetry signals transmitted by way of transcutaneous narrowband inductive links may be implemented by a cochlear implant communicatively coupled to a sound processor, or by a sound processor communicatively coupled to a cochlear implant.

For instance, an exemplary cochlear implant may include a cochlear implant coil configured, when the cochlear implant is implanted within a recipient, to form a transcutaneous narrowband inductive link with a sound processor coil associated with a sound processor operating externally to the recipient. As in the exemplary system described above, the cochlear implant coil in this example may have a size larger than a size of the sound processor coil and may enable the cochlear implant to receive, from the sound processor by way of the transcutaneous narrowband inductive link, a forward telemetry signal incorporating both 1) power for powering operations of the cochlear implant, and 2) forward telemetry data for directing the operations of the cochlear implant. The cochlear implant may further include equalization circuitry communicatively coupled with the cochlear implant coil and configured, when the cochlear implant is implanted within the recipient, to receive the forward telemetry signal by way of the cochlear implant coil and to facilitate recovery of the forward telemetry data from the forward telemetry signal by compensating for distortion introduced onto the forward telemetry signal as a result of bandwidth limitations imposed by the transcutaneous narrowband inductive link.

As another exemplary implementation, an exemplary sound processor may include a sound processor coil configured, when the sound processor operates externally to a recipient, to form a transcutaneous narrowband inductive link with a cochlear implant coil of a cochlear implant implanted within the recipient. As in other examples described above, the sound processor coil may have a size smaller than a size of the cochlear implant coil so that the sound processor is enabled to transmit, to the cochlear implant by way of the transcutaneous narrowband inductive link, a forward telemetry signal. As with the forward telemetry signals described above, this forward telemetry signal may incorporate both 1) power for powering operations of the cochlear implant, and 2) forward telemetry data for directing the operations of the cochlear implant. The sound processor may further include equalization circuitry communicatively coupled with the sound processor coil and configured, prior to transmission of the forward telemetry signal by way of the sound processor coil, to compensate the forward telemetry signal for distortion that is to be introduced onto the forward telemetry signal as a result of bandwidth limitations imposed by the transcutaneous narrowband inductive link. In this way, the equalization circuitry may facilitate the cochlear implant in recovery of the forward telemetry data from the forward telemetry signal when the signal is received and processed by the cochlear implant.

The systems and methods described herein for equalizing telemetry signals transmitted by way of a transcutaneous narrowband inductive link may provide various benefits. Some of these benefits arise from the ability of the systems and devices described herein to relax the requirements for the physical and geometric positioning of the sound processor coil and the cochlear implant coil while power and data are transferred. When coils are inductively coupled together to form an inductive link, a coupling coefficient and a quality factor (commonly referred to as a "Q factor" or "Q value") characterize various attributes of the coupling between the coils, including bandwidth limitations imposed by the inductive link. When the geometric relationship of the coils is such that the coils are relatively far apart and/or poorly aligned (e.g., which may be the case if a headpiece and associated magnetics are excluded from the system for convenience), the coupling coefficient of the link may become diminished. This causes power transfer to occur outside of a critical coupling region that provides the most efficient power transfer. To some extent, the power transfer may be optimized by operating the coils at higher loaded Q factors that help retain the critical coupling operating point. However, the higher Q factors of the coils may have the effect of limiting the bandwidth of the link, thereby distorting data information transferred over the link to the point that the link is unusable for transferring data above a particular data rate (e.g., a data rate needed for proper functionality of a cochlear implant system). Accordingly, maintaining a wide bandwidth and efficient power transfer at large coil separations (e.g., without use of separate headpiece and magnetic components) has conventionally been challenging.

Due to such challenges, conventional systems have typically provided a suitably wide bandwidth for the high data rates needed for cochlear implant operations by making provision for strict geometric limitations to be adhered to. For example, by integrating an external coil within a headpiece that can be positioned on the head independently from a sound processor, conventional systems have used magnetic components to ensure that a headpiece is continuously positioned and aligned, with respect to an implanted coil, in an ideal manner that facilitates efficient power transfer and wide bandwidth. Additionally, certain conventional systems have been designed to utilize a relatively high carrier frequency (e.g., 49 MHz or higher) for the inductive link because a high carrier frequency naturally allows for a relatively large bandwidth over which data may be transferred. Unfortunately, while these conventional approaches enable cochlear implant data rates by providing wideband inductive links, the approaches are also non-ideal in certain respects. For example, it is not necessarily desirable for a cochlear implant system to require a headpiece that is separately housed from a sound processor due to inconvenience to the recipient; aesthetics desired by the recipient; cost of the headpiece, cable, and magnetic components; and so forth. Moreover, a 49 MHz carrier frequency may be relatively inefficient from a power usage perspective.

Other conventional systems have addressed the challenges described above by way of other approaches. For example, certain medical systems and devices (e.g., systems and devices other than cochlear implant systems and devices) may be able to properly operate with slower data transmission rates that require narrower bandwidths. Other systems and devices may bifurcate power transmission from data transmission by employing separate transmission channels for power and data rather than combining data and power on a single channel. This type of approach requires additional frequency division hardware and may raise additional challenges of its own.

Fortunately, systems and devices described herein for equalizing telemetry signals transmitted by way of a transcutaneous narrowband inductive link allow for the elimination of headpiece, cable, and magnetic components, all while providing reliable, full-duplex data and power transfer at data rates suitable for cochlear implant system functionality, and in a smaller, less expensive system. In this way, systems and devices described herein may allow for combined data and power transfer at a relatively high data rates (e.g., greater than 1.0 megabits per second (Mbps)) using a relatively low carrier frequency (e.g., lower than 49 MHz), may reduce or eliminate magnet retention issues and warranty costs for cable replacement issues, and may increase the convenience and aesthetic appeal experienced by recipients who no longer need a headpiece to be magnetically coupled to their heads. Moreover, the systems and devices described herein may reduce driver losses to increase power transfer efficiency and system battery life even with reduced geometric alignment and spacing requirements for the coils, may make use of a carrier frequency that has international regulatory approval (e.g., an RFID spectral allocation or the like), and may reduce component count (e.g., due to orthogonal signaling with channel sharing) to decrease the overall cost and/or size of the cochlear implant system. All of these and other benefits may be provided while present data formats and telemetry rates are maintained, thus allowing legacy protocols to continue to be used.

Moreover, all of the potential drawbacks described above to be associated with conventional approaches may be avoided. For example, systems and methods described herein may provide equalization that reduces the need for low loaded coil Q factors to be maintained (in order to maintain data bandwidth) such that the power transfer can be properly optimized. For example, by using dissimilar coil diameters, systems and devices described herein may provide higher loaded coil Q factors to perform efficient power transfer while still allowing data to be reliably transferred at high data rates over a transcutaneous narrowband inductive link associated with the lower carrier frequency.

Various embodiments will now be described in more detail with reference to the figures. The disclosed systems and methods may provide one or more of the benefits mentioned above and/or various additional and/or alternative benefits that will be made apparent herein.

FIG. 1 illustrates an exemplary cochlear implant system 100 that may implement or incorporate one or more of the systems and devices described herein for equalizing telemetry signals transmitted by way of a transcutaneous narrowband inductive link. For instance, systems and devices described herein may be implemented by cochlear implant system 100 in the form illustrated in FIG. 1, in an alternative form described herein, in another form as may serve a particular implementation, or by an implementation of a particular component of cochlear implant system 100. While the examples described herein relate specifically to cochlear implant systems such as cochlear implant system 100 and various implementations thereof, it will be understood that principles described herein may be advantageously applied, in various embodiments, to other types of systems and devices besides cochlear implant systems and devices. For example, other medical systems and devices such as heart pacemakers, deep brain simulators, urinary incontinence devices, and other systems and devices that make use of transcutaneous inductive links may also advantageously implement any of the principles described herein for equalizing telemetry signals transmitted by way of a transcutaneous narrowband inductive link. In such examples, for instance, any suitable type of implantable device may perform communication and equalization-related operations described herein as being performed by cochlear implants, and any suitable type of external device may perform communication and equalization-related operations described herein as being performed by sound processors and/or headpieces.

As shown, cochlear implant system 100 may include various components configured to be located external to a cochlear implant recipient including, but not limited to, an audio input device 102, a sound processor 104, and a headpiece 106. Cochlear implant system 100 may further include various components configured to be implanted within the recipient including, but not limited to, a cochlear implant 108 (also referred to as an implantable cochlear stimulator) and a lead 110 (also referred to as an intracochlear electrode array) with a plurality of electrodes 112 disposed thereon. In certain examples, additional, fewer, or alternative components may be included within cochlear implant system 100 as may serve a particular implementation. The components shown in FIG. 1 will now be described in more detail.

Audio input device 102 may be configured to detect audio signals presented to the recipient. Audio input device 102 may be implemented in any suitable manner. For example, audio input device 102 may include or be implemented by a microphone such as a T-MIC™ microphone from Advanced Bionics. Such a microphone may be associated with a particular ear of the recipient such as by being located in a vicinity of the particular ear (e.g., within the concha of the ear near the entrance to the ear canal) or held within the concha of the ear near the entrance of the ear canal by a boom or stalk that is attached to an ear hook configured to be selectively attached to sound processor 104, In other examples, audio input device 102 may be implemented by one or more microphones disposed within headpiece 106, one or more microphones disposed within sound processor 104, one or more omnidirectional microphones with substantially omnidirectional polar patterns, one or more directional microphones, one or more beam-forming microphones (e.g., omnidirectional microphones combined to generate a front-facing cardioid polar pattern), and/or any other suitable microphone or microphones as may serve a particular implementation. Additionally or alternatively, audio input device 102 may be implemented as an audio source other than the microphones described above. For instance, audio input device 102 may be implemented as a telecoil, as a digital device (e.g., a Bluetooth device, an FM device, a mobile device, a media player device, etc.) providing prerecorded audio or audio received from an audio source such as a digital media service, as a remote microphone that captures and transmits an audio input signal, and/or as any other suitable source of an audio signal that may be presented to the recipient in a particular implementation.

Sound processor 104 may be configured to direct cochlear implant 108 to generate and apply electrical stimulation (also referred to herein as "stimulation current") representative of one or more audio signals (e.g., one or more audio signals provided by audio input device 102) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. While, for the sake of simplicity, electrical stimulation will be described herein as being applied to one or both of the cochleae of a recipient, it will be understood that stimulation current may also be applied to other suitable nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. In some examples, sound processor 104 may provide to the recipient both electrical stimulation (by way of cochlear implant 108, lead 110, and electrodes 112) and acoustic stimulation (by way of a loud speaker not explicitly shown in FIG. 1) to leverage residual hearing that the recipient may have in certain frequency ranges or the like.

In some examples, sound processor 104 may wirelessly transmit power and/or forward telemetry data (e.g., stimulation parameters in the form of data words, etc.) to cochlear implant 108 by way of a transcutaneous inductive link 114 (also referred to as wireless communication link 114) between headpiece 106 and cochlear implant 108. It will be understood that inductive link 114 may include a bidirectional (i.e., full-duplex) communication link and/or one or more dedicated unidirectional (i.e., half-duplex) communication links. In some examples, sound processor 104 may execute and operate in accordance with a sound processing program that has been loaded into memory contained within sound processor 104.

Headpiece 106 may be communicatively coupled to sound processor 104 and may include an antenna (e.g., an inductive coil, etc.) used for forming inductive link 114 to facilitate wireless coupling of sound processor 104 to cochlear implant 108. As will be described in more detail below, headpiece 106 may be excluded from certain implementations of cochlear implant system 100 if sound processor 104 itself contains an inductive coil and provisions are made to ensure that power and telemetry data can be transmitted at suitable efficiencies and rates for proper functionality of the system. In embodiments that do include headpiece 106, however, it will be understood that headpiece 106 may be configured to be affixed to the recipient's head and positioned such that the coil housed within headpiece 106 is communicatively coupled to a corresponding implantable coil included within or otherwise associated with cochlear implant 108. As such, headpiece 106 and cochlear implant 108 may include magnetic components to enable the attachment of headpiece 106 to the head of the recipient, and headpiece 106 and sound processor 104 may include communicative components (e.g., a cable, respective communication interface components, etc.) to enable sound processor 104 to communicate the power and data by way of the coil in headpiece 106. In any case, whether or not headpiece 106 is included or designed around in a particular implementation, power and data signals may be wirelessly transmitted between sound processor 104 and cochlear implant 108 via inductive link 114.

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by audio input device 102) in accordance with one or more stimulation parameters transmitted thereto by sound processor 104. Cochlear implant 108 may be further configured to apply the electrical stimulation to one or more stimulation sites within the recipient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously or concurrently by way of multiple electrodes 112.

Figure 2:
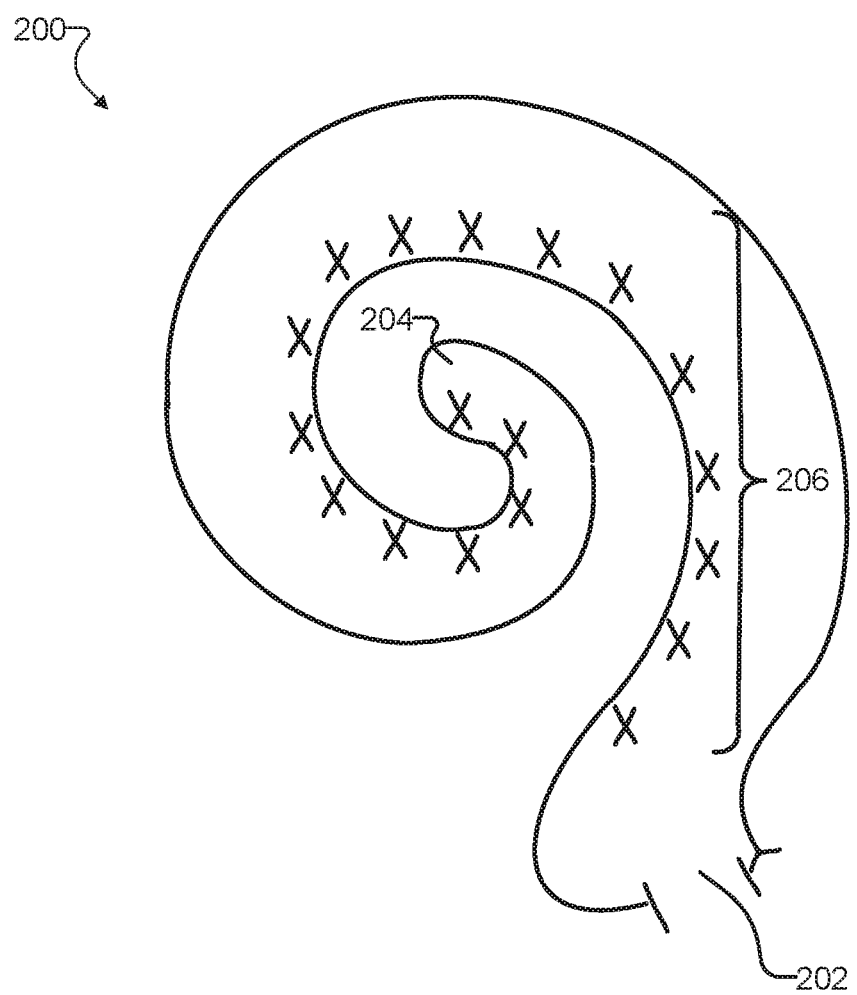
FIG. 2 illustrates a schematic structure of the human cochlea.

FIG. 2 illustrates a schematic structure of human cochlea 200 into which lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. Auditory nerve tissue 206 within cochlea 200 is distributed and arranged in a tonotopic manner. That is, relatively low frequencies are encoded at or near apex 204 of cochlea 200 (referred to as an "apical region") while relatively high frequencies are encoded at or near base 202 (referred to as a "basal region"). Hence, each location along the length of cochlea 200 corresponds to a different perceived frequency. Cochlear implant system 100 may therefore be configured to apply electrical stimulation to different locations within cochlea 200 (e.g., different locations along auditory nerve tissue 206) to provide a sensation of hearing to the recipient. For example, when lead 110 is properly inserted into cochlea 200, each of electrodes 112 may be located at a different cochlear depth within cochlea 200 (e.g., at a different part of auditory nerve tissue 206) such that stimulation current applied to one electrode 112 may cause the recipient to perceive a different frequency than the same stimulation current applied to a different electrode 112 (e.g., an electrode 112 located at a different part of auditory nerve tissue 206 within cochlea 200).

Figure 3:
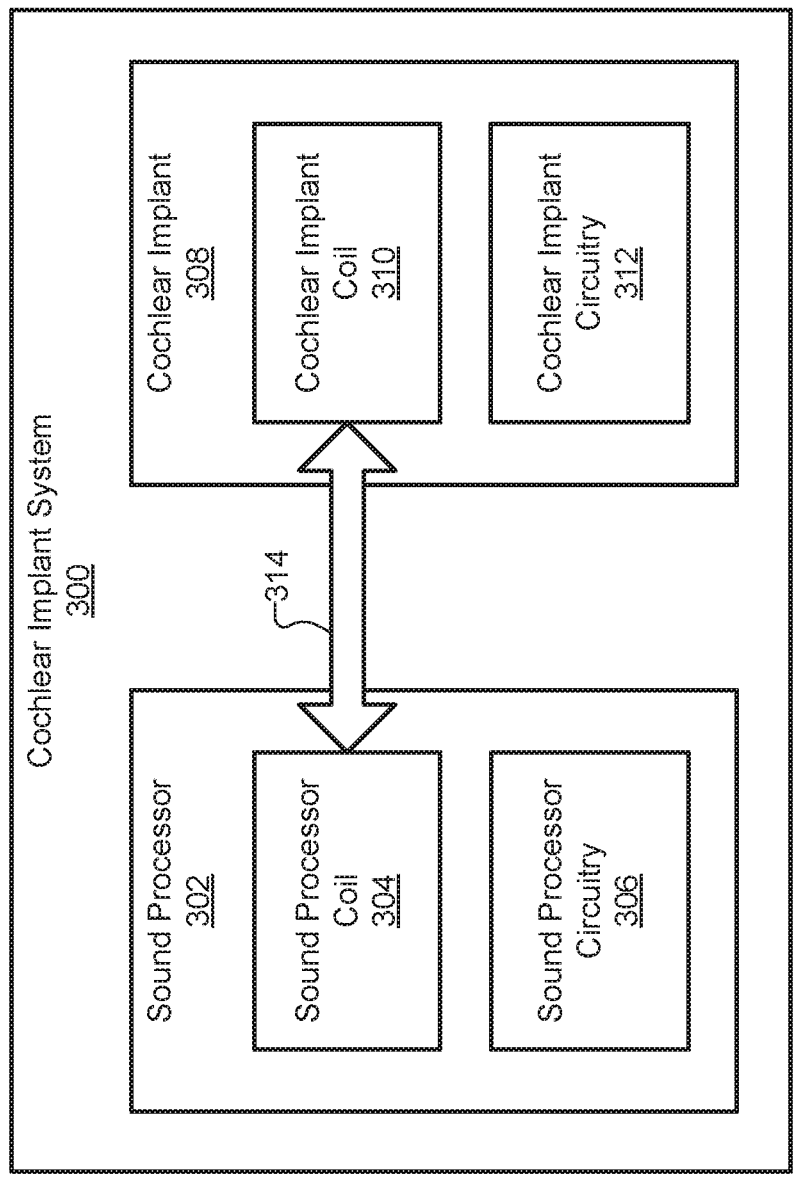
FIG. 3 illustrates an exemplary system for equalizing telemetry signals transmitted by way of a transcutaneous narrowband inductive link according to principles described herein.

Cochlear implant system 100 described above will be understood to represent a generic cochlear implant system 100 that may or may not be configured to equalize telemetry signals transmitted by way of a transcutaneous narrowband inductive link in accordance with systems and devices described herein. In contrast, FIG. 3 illustrates certain components of an exemplary cochlear implant system 300 ("system 300") that specifically represents an implementation of cochlear implant system 100 configured to equalize telemetry signals transmitted by way of a transcutaneous narrowband inductive link according to principles described herein. Specifically, as shown, system 300 includes a sound processor 302 that may implement sound processor 104 described above. Sound processor 302 is shown to include a sound processor coil 304 and sound processor circuitry 306, and, as such, it will be understood that sound processor 302 may also implement headpiece 106 (i.e., by performing the functions described above to be performed by headpiece 106) for implementations in which headpiece 106 is excluded from the cochlear implant system so as to provide one or more of the benefits described above.

System 300 further includes a cochlear implant 308 that may implement cochlear implant 108 (as well as other internal components such as lead 110 and electrodes 112) described above. As shown, cochlear implant 308 may include a cochlear implant coil 310 and cochlear implant circuitry 312. As shown, sound processor 302 and cochlear implant 308 are communicatively coupled within system 300 by way of a transcutaneous narrowband inductive link 314 ("narrowband link 314") between sound processor coil 304 and cochlear implant coil 310. Narrowband link 314 will be understood to implement inductive link 114, described above, for this particular cochlear implant system implementation.

While the description herein focuses on the systems and devices themselves that equalize telemetry signals transmitted by way of a transcutaneous narrowband inductive link, it will be understood that such systems and devices may operate by performing methods for equalizing telemetry signals transmitted by way of a transcutaneous narrowband inductive link. Specifically, for example, system 300 may be configured to perform a method that includes one or more of the following method operations performed in the following sequence or another suitable sequence (e.g., including a sequence in which one or more of the operations are performed concurrently). As one operation of the method, cochlear implant coil 310 may form narrowband link 314 with sound processor coil 304, which, as described below, may have a size smaller than a size of cochlear implant coil 310. In this way, cochlear implant 308 may be configured to perform a method operation of receiving, from sound processor 302 by way of narrowband link 314, a forward telemetry signal incorporating power for powering operations of the cochlear implant and forward telemetry data for directing the operations of the cochlear implant. As another operation of the method, equalization circuitry implemented in sound processor circuitry 306 and/or cochlear implant circuitry 312 may receive and process the forward telemetry signal transmitted over narrowband link 314. As such, another operation of the method involves the equalization circuitry facilitating recovery of the forward telemetry data from the forward telemetry signal by compensating for distortion introduced onto the forward telemetry signal as a result of bandwidth limitations imposed by narrowband link 314.

In accordance with this method and other similar methods for equalizing telemetry signals that may be performed by implementations of cochlear implant system 300, each of the components of system 300 will now be described in more detail.

Sound processor 302 may be configured to operate externally to a recipient of system 300. For example, sound processor 302 may be configured to be a behind-the-ear sound processor (i.e., a sound processor that uses an ear hook to hang on the pinna and be worn behind the pinna), an off-the-ear sound processor (i.e., a sound processor that is worn on the head in a location other than behind the ear, such as being magnetically coupled to the head so as to leave the space behind the pinna free), a body-worn sound processor (i.e., a sound processor that is worn or carried off the head such as by attaching to clothing or being carried in a pocket), or any other suitable type of sound processor that is worn in any suitable manner.

Sound processor coil 304 may be configured, when sound processor 302 operates externally to the recipient, to form narrowband link 314 with cochlear implant coil 310 of cochlear implant 308 implanted within the recipient. To this end, sound processor coil 304 may be configured to have a size that is smaller than a size of cochlear implant coil 310, and may enable sound processor 302 to transmit, to cochlear implant 308 by way of narrowband link 314, a forward telemetry signal that incorporates power for powering operations of cochlear implant 308 and forward telemetry data for directing the operations of cochlear implant 308.

Figure 4A:
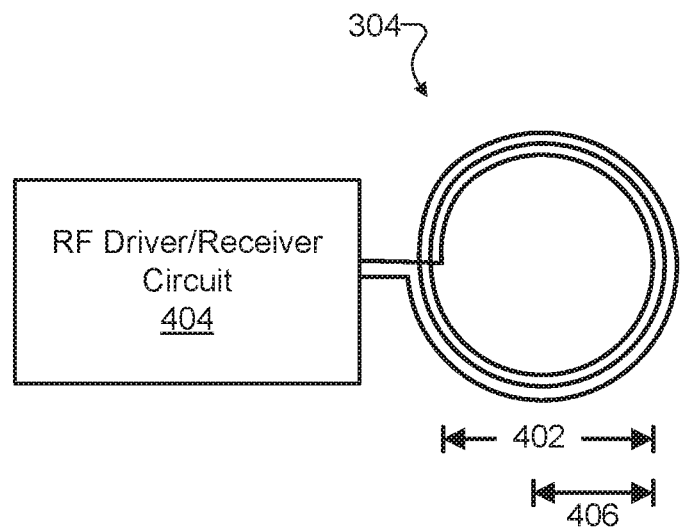
FIGS. 4A and 4B illustrate exemplary aspects of inductive coils and other corresponding components that may be used to form a transcutaneous narrowband inductive link according to principles described herein.

To illustrate, FIG. 4A illustrates exemplary aspects of an implementation of sound processor coil 304 including a size 402 of coil 304. FIG. 4A further illustrates a corresponding radio frequency ("RF") driver/receiver circuit 404 that may be used together with sound processor coil 304 to form narrowband link 314, Because the exemplary implementation of sound processor coil 304 in FIG. 4A is shown to be a circular coil of wire (or a printed circuit trace, etc.) arranged in a planar spiral, size 402 of sound processor coil 304 is shown in this example to be a diameter of sound processor coil 304. For instance, size 402 may represent an inner diameter of the coil (i.e., a diameter of the smallest loop of the coil), an outer diameter of the coil (i.e., a diameter of the largest loop of the coil), an average diameter of the coil, or the like. In other implementations, size 402 may be defined in other suitable ways. For instance, a radius 406 of the circle could be used instead of the diameter of size 402, or, in implementations using non-planar coils wound around a core, stacked layers of planar coils, or the like, a coil height or winding layer quantity or other such characteristic may be used instead of or in addition to the diameter in defining size 402. Additionally, if sound processor coil 304 is implemented as a non-circular coil (e.g., a square, rectangular, elliptical, or other shape of coil), size 402 may be implemented as a length, width, radius, minor diameter, major diameter, or other characteristic of the windings of the coil as may serve a particular implementation. Additionally, in certain examples, size 402 may be implemented as a two-dimensional area of the coil's windings, rather than as a one-dimensional vector such as the diameter, radius, or length. RF driver/receiver circuit 404 may be directly connected to sound processor coil 304 and configured to use sound processor coil 304 as an antenna to transmit and/or receive wireless RF signals.

When coils forming an inductive link such as narrowband link 314 have dissimilar sizes (e.g., when the size of cochlear implant coil 310 is significantly larger than the size of sound processor coil 304), undesirable effects of the separation of the coils can be mitigated to improve power transfer. As mentioned above, for example, one such effect caused by this geometry in which the coil sizes are dissimilar is that of limiting the maximum attainable coupling coefficient for the inductive link. However, when operated at a high Q factor, a link design may cause the coupling coefficient to be more stable and constant even if the spacing and/or alignment of the coils are suboptimal (e.g., which may be the case if a magnetically attached headpiece such as headpiece 106 is excluded or integrated into a sound processor such as sound processor 302). By stabilizing the coupling coefficient in this manner, the resulting inductive link may be operated at or near the critical coupling region where power transfer is most efficient, albeit with a narrower bandwidth that causes link 314 to be a relatively "narrowband" inductive link. Thus, while this size disparity between coils 304 and 310 enables high power efficiency and other related benefits even with suboptimal spacing and alignment (e.g., thereby enabling the exclusion of a dedicated headpiece), it is the equalization circuitry described herein that will resolve the bandwidth issues that are caused by the coil size disparity and that otherwise would limit the data rate of data that can be transferred over narrowband link 314.

Returning to FIG. 3, sound processor circuitry 306 may include circuitry configured to perform the functionality of sound processor 302 and to use sound processor coil 304 to communicate with cochlear implant 308. More particularly, sound processor circuitry 306 may be configured to perform the same or similar functions as described above with respect to sound processor 104, including, for instance, functions for processing incoming audio signals (e.g., from an audio input device such as audio input device 102, not explicitly shown in FIG. 3) and communicating with cochlear implant 308 using narrowband link 314 to direct cochlear implant 308 to apply stimulation to a recipient in a manner that stimulates a sensation of hearing in the recipient. In order to perform such functionality, sound processor circuitry 306 may include analog or digital circuitry such as a battery, a power supply and associated power control circuits, a modulation controller, an RF driver circuit (e.g., a combination driver/receiver circuit such as RF driver/receiver circuit 404), computing components (e.g., one or more processors, memories, etc.), and/or any other suitable components and circuitry as may serve a particular implementation.

Moreover, along with including the circuitry described above, sound processor circuitry 306 may further include, in certain implementations, equalization circuitry configured to facilitate recovery of signals that are to be transmitted to cochlear implant 308 and/or that have been received from cochlear implant 308 (in examples where system 300 implements full-duplex communications). For example, referring to forward telemetry signals (i.e., telemetry signals transmitted from sound processor 302 to cochlear implant 308), such equalization circuitry may be configured to facilitate recovery, by cochlear implant 308, of forward telemetry data from a forward telemetry signal by compensating, prior to transmission of the forward telemetry signal by way of sound processor coil 304, for distortion that is anticipated to be introduced onto the forward telemetry signal as a result of bandwidth limitations imposed by narrowband link 314. As will be described in more detail below, equalization circuitry for backward telemetry signals (i.e., telemetry signals transmitted from cochlear implant 308 to sound processor 302) may similarly be integrated within sound processor 302 in certain implementations.

Sound processor 302 may be implemented within a single housing. That is to say, rather than spreading different components of sound processor 302 into distinct housings (e.g., a housing configured to be worn behind the ear for sound processor circuitry 306 and a headpiece housing configured to attach magnetically to the head in an off-ear location for sound processor coil 304), sound processor coil 304 and sound processor circuitry 306 may both be integrated into the single housing (e.g., a single behind-the-ear housing, a single off-the-ear housing, etc.) of sound processor 302 such that narrowband link 314 does not employ a dedicated headpiece (i.e., a headpiece associated with sound processor 302 and housed in a separate housing from the sound processor). As has been mentioned, eliminating the need for a separate headpiece housed separately from the single housing of the sound processor may result in various significant benefits. For example, it may be more convenient and aesthetically desirable to the recipient to wear a single sound processor (e.g., a relatively discreet sound processor tucked behind the ear) than to wear a sound processor/headpiece combination in which a cable runs from the sound processor to the headpiece on a different part of the head. As another example, the need for various components (e.g., the headpiece housing, the cable, internal and external magnetic components facilitating the placement of the headpiece, etc.) may be eliminated by the exclusion of the headpiece, thereby making the entire system smaller, more attractive, and more cost effective to the recipient.

Cochlear implant 308 may be configured to be implanted within the recipient of system 300, and to operate internally to the recipient. For example, as will be described in more detail below, cochlear implant 308 may interoperate with sound processor 302 to perform the functionality described above with respect to cochlear implant system 100 to enable and facilitate the recipient in perceiving sound presented to the recipient.

Cochlear implant coil 310 may be configured, when cochlear implant 308 is implanted within the recipient, to form narrowband link 314 with sound processor coil 304 associated with sound processor 302 operating externally to the recipient. To this end, as mentioned above, cochlear implant coil 310 may be configured to have a size that is larger than a size of sound processor coil 304 so as to thereby enable cochlear implant 308 to receive, from sound processor 302 by way of narrowband link 314, the forward telemetry signal incorporating power for powering operations of cochlear implant 308 and forward telemetry data for directing the operations of cochlear implant 308.

Figure 4B:
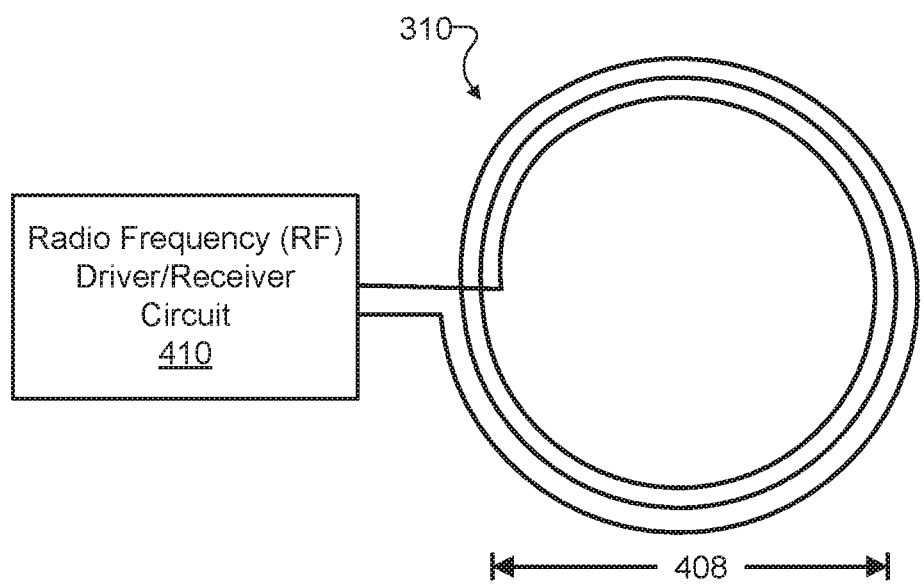

To illustrate, FIG. 4B illustrates exemplary aspects of cochlear implant coil 310 including a size 408 of cochlear implant coil 310. Similar to FIG. 4A described above, FIG. 4B further illustrates a corresponding RF driver/receiver circuit 410 that may be used together with cochlear implant coil 310 to form narrowband link 314. Size 408 of sound processor coil 310 is shown to be a diameter of cochlear implant coil 310 in this example in which cochlear implant coil 310 is implemented as a circular coil of wire (or a printed circuit trace, etc.) arranged in a planar spiral. It will be understood however, that size 408, like size 402 described above, may be defined in other suitable ways for examples in which cochlear implant coil 310 is implemented by other shapes or the like. While it will be understood that size 402 and size 408 of coils 304 and 310, respectively, are not necessarily drawn to scale, size 408 of cochlear implant coil 310 may be understood to be significantly larger than size 402 of sound processor coil 304, as depicted in FIGS. 4A and 4B. RF driver/receiver circuit 410 may be directly connected to cochlear implant coil 310 and configured to use cochlear implant coil 310 as an antenna to transmit and/or receive wireless RF signals.

Returning to FIG. 3, cochlear implant circuitry 312 may include circuitry configured to perform the functionality of cochlear implant 308 and to use cochlear implant coil 310 to communicate with sound processor 302. More particularly, cochlear implant circuitry 312 may be configured to perform the same or similar functions as described above with respect to cochlear implant 108, including, for instance, functions for communicating with sound processor 302 using narrowband link 314 to receive and carry out instructions to apply stimulation to a recipient in a manner that stimulates a sensation of hearing in the recipient (e.g., by way of an electrode lead such as lead 110, not explicitly shown in FIG. 3). In order to perform such functionality, cochlear implant circuitry 312 may include analog or digital circuitry such as power control circuits, current generator circuits, an RF receiver driver circuit (e.g., a combination driver/receiver circuit such as RF driver/receiver circuit 410), and/or any other suitable components and circuitry as may serve a particular implementation.

Moreover, along with including the circuitry described above, cochlear implant circuitry 312 may further include, in certain implementations, equalization circuitry configured to facilitate recovery of signals that have been received by cochlear implant 308 and/or that are to be transmitted to sound processor 302 (in examples where system 300 implements full-duplex communications). For example, referring to forward telemetry signals, such equalization circuitry may be configured to receive the forward telemetry signal by way of cochlear implant coil 310 and to facilitate recovery of the forward telemetry data from the forward telemetry signal by compensating for distortion introduced onto the forward telemetry signal as a result of bandwidth limitations imposed by narrowband link 314. As will be described in more detail below, equalization circuitry for backward telemetry signals may similarly be integrated with cochlear implant 308 in certain implementations.

As described above, narrowband link 314 may be a transcutaneous narrowband inductive link that is "narrowband" due, at least in part, to the size differential between sound processor coil 304 and cochlear implant coil 310 and the higher Q factors and reduced bandwidth that result from designing the circuitry to retain power efficiencies even when spacing and alignment requirements for the coils are relaxed. As further mentioned above, equalization circuitry may be used to allow not only for geometric spacing and alignment requirements to be more flexible but also to allow for the operating frequency (i.e., the carrier frequency used by narrowband link 314) to be reduced from a relatively high frequency like 49 MHz to a lower frequency such as the 13.56 MHz frequency that has international regulatory approval for ISM/RFID usage, or another suitable frequency as may serve technical, regulatory, and/or other interests of a particular implementation.

To explain how equalization circuitry integrated within sound processor circuitry 306 and/or cochlear implant circuitry 312 can facilitate recovery of telemetry data by compensating for distortion introduced onto telemetry signals as a result of bandwidth limitations imposed by narrowband link 314, an exemplary forward telemetry signal will now be illustrated and described.

Figure 5:
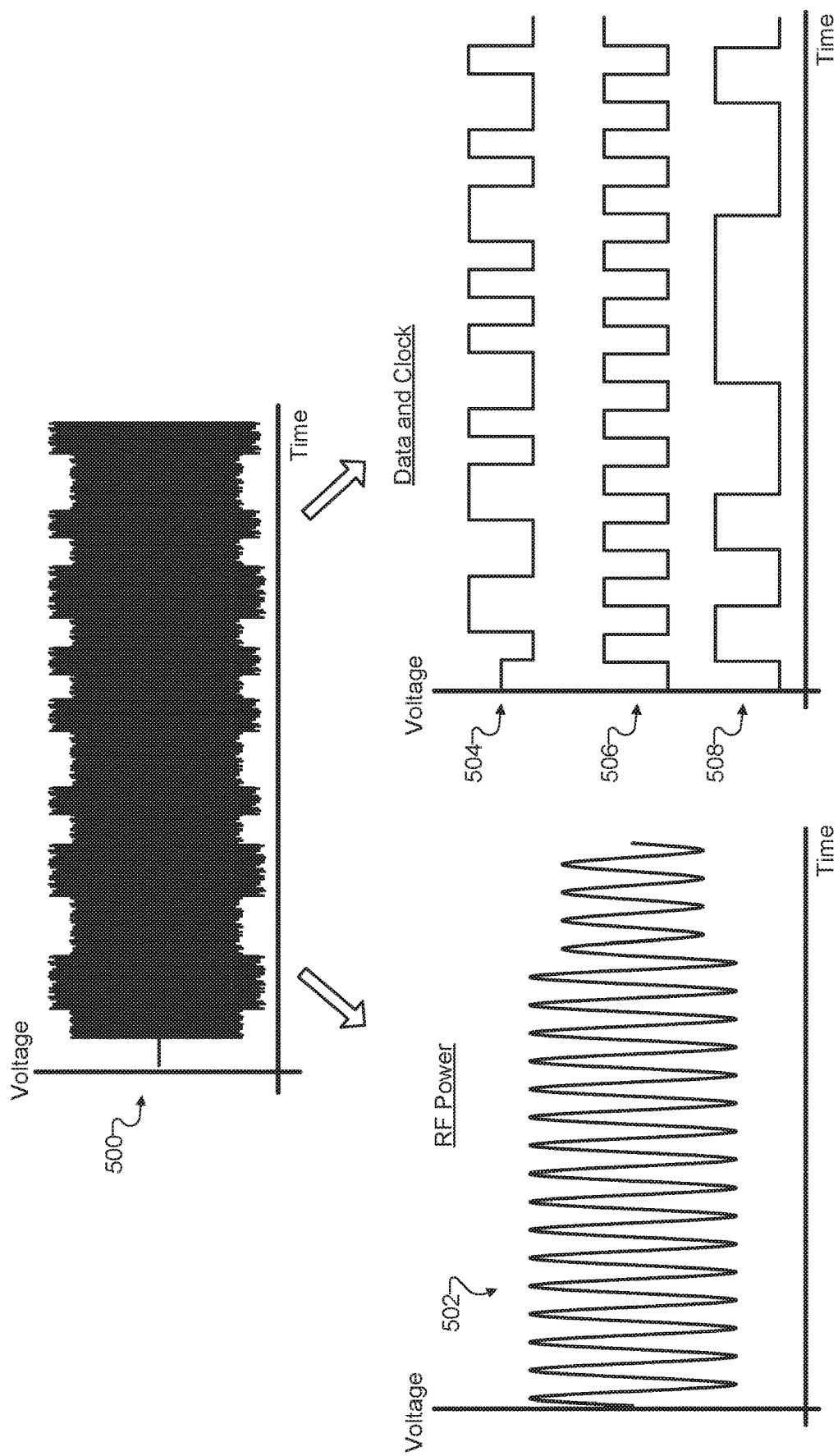
FIG. 5 illustrates an exemplary forward telemetry signal and certain incorporated components thereof according to principles described herein.

Specifically, FIG. 5 shows an exemplary forward telemetry signal 500 and certain incorporated components thereof. Forward telemetry signal 500 is depicted in FIG. 5 to modulate, onto a carrier wave at an RF frequency, forward telemetry data represented using an amplitude shift keying ("ASK") modulation protocol. Specifically, forward telemetry signal 500 is shown to have been generated using an ASK protocol whereby power is delivered as RF power at a carrier frequency and forward telemetry data is modulated onto the RF power by adjusting an amplitude of the RF power in a manner that represents digital values of the forward telemetry data. Accordingly, as shown, forward telemetry signal 500 is depicted over the course of a large number of periods of the carrier wave such that the varying amplitude of the signal may be seen to go up and down in accordance with the forward telemetry data modulated onto the signal. For example, as will be described in more detail below, the carrier wave may be transmitted at a 100% amplitude to represent one digital value (e.g., a binary '1' in certain examples), and may be transmitted at a reduced amplitude (e.g., an 80% or 90% amplitude or another suitable amplitude less than 100%) to represent a different digital value (e.g., a binary '0' in certain examples).

While forward telemetry signal 500 illustrates an ASK modulation scheme, it will be understood that, in certain examples, other modulation schemes may be used. For example, an on-off keying ("OOK") modulation protocol may be employed to turn the carrier wave on (at a full amplitude) to represent one digital value such as a binary '1', and to turn the carrier wave off to represent another digital value such as a binary '0'. In other words, an OOK modulation may be conceived of as an ASK modulation in which the index of modulation is 100% because the amplitude envelope of the carrier wave oscillates between 100% and 0%. In many examples, it may be preferable to use ASK modulation with a lower index of modulation (e.g., a 10% index of modulation in which the amplitude envelope oscillates between 100% and 90%, a 15% index of modulation in which the amplitude envelope oscillates between 100% and 85%, etc.). Not only does a lower index of modulation allow for power to be transmitted more efficiently (since at least some power is always transmitted, rather than power only being turned on for one digital value and then being turned off for the other), but a lower index of modulation further helps minimize side band levels so that forward telemetry data may experience less distortion when carried over a narrowband link.

While signal 500 in FIG. 5 is a forward telemetry signal that incorporates power for powering operations of the cochlear implant and forward telemetry data for directing operations of the cochlear implant, it will be understood that cochlear implant coil 310 may further enable cochlear implant 308 to transmit, to sound processor 302 by way of narrowband link 314, a backward telemetry signal incorporating backward telemetry data.

To illustrate, FIG. 6A shows an exemplary half-duplex implementation 600-A of system 300 in which narrowband link 314 is configured only to carry forward telemetry signals such as forward telemetry signal 500, while FIG. 6B shows an exemplary full-duplex implementation 600-B of system 300 in which narrowband link 314 is configured to carry both forward telemetry signals and backward telemetry signals. As shown, in implementation 500-A, sound processor 302 includes transmitter circuitry 602 for transmitting a forward telemetry signal, but lacks receiver circuitry for receiving a backward telemetry signal, and cochlear implant 308 correspondingly includes receiver circuitry 604 for receiving the forward telemetry signal while lacking transmitting circuitry for transmitting the backward telemetry signal. In contrast, in implementation 600-B, sound processor 302 includes both transmitter circuitry 602 and receiver circuitry 606, thereby allowing both forward telemetry signals and backward telemetry signals to be communicated. Similarly, in implementation 600-B, cochlear implant 308 includes both receiver circuitry 604 and transmitter circuitry 608, thereby allowing for the communication of both the forward telemetry signals and backward telemetry signals.

Just as forward telemetry data may be representative of any suitable information that is useful to communicate from sound processor 302 to cochlear implant 308 in a particular implementation (e.g., instructions directing cochlear implant 308 to apply appropriate stimulation to a recipient to induce a sense of hearing in the recipient), backward telemetry data may be representative of any suitable information that is useful to communicate back from cochlear implant 308 to sound processor 302. For instance, backward telemetry data may be representative of acknowledgments by cochlear implant 308 of instructions provided by sound processor 302, error codes associated with issues experienced by cochlear implant 308, data detected by cochlear implant 308, status reports for cochlear implant 308, and/or any other suitable information as may serve a particular implementation.

In various examples, backward telemetry signals transmitted by cochlear implant 308 may have certain commonalities and differences with a forward telemetry signals such as forward telemetry signal 500. For example, as one commonality, an ASK or OOK modulation scheme may be used to transfer backward telemetry data in a similar manner as described above for transferring forward telemetry data. However, as one exemplary difference resulting from the fact that cochlear implant 308 is powered by sound processor 302 (e.g., via power incorporated in forward telemetry signal 500), a backward telemetry signal sent back from cochlear implant 308 may rely on the power that was provided by sound processor 302 rather than transmitting power back to sound processor 302.

Referring to the full-duplex implementation 600-B in FIG. 6B, the carrier frequencies used by narrowband link 314 for the forward telemetry signal and backward telemetry signal to be communicated may be any suitable frequencies. For instance, because there may be significantly more forward telemetry data that needs to be communicated than backward telemetry data, it may be desirable in certain implementations for different carrier frequencies (e.g., carrier frequencies individually customized to the different needs of the forward and backward telemetry links) to be employed. A higher carrier frequency may be used for the forward telemetry signal than for the backward telemetry signal, for example, because the higher carrier frequency may offer a wider bandwidth over which the large amount of data may be transferred at a higher data rate than would normally be associated with a lower carrier frequency.

On the other hand, for various reasons that have been described, it may be desirable in certain implementations for even the forward telemetry signal to use a relatively low carrier frequency as long as forward telemetry data can still be reliably communicated at a suitable data rate. Accordingly, in these examples, forward telemetry signals and backward telemetry signals may both be transmitted orthogonally on different channels of a same carrier frequency. For example, full duplex operation may be performed by separating amplitude and phase modulation sub-channels, by separating data channel rates by frequency (e.g., using frequency-division multiplexing), and/or by otherwise communicating multiple data streams using the same carrier frequency in any suitable manner. In these examples, an ASK modulation with a low modulation index may be implemented for the forward telemetry signal using pulse width modulation and/or out-phasing in the RF driver circuitry, while backward telemetry signal reactance modulation by cochlear implant 308 may introduce very little amplitude ripple in the forward telemetry channel so as not to dissipate coupled power.

By sharing a same carrier frequency for forward telemetry and backward telemetry channels of a full-duplex implementation of narrowband link 314 in these ways, various benefits may be realized. For example, each of the advantages described above in relation to lower carrier frequencies may be attained. Moreover, the transmitter and receiver circuitry implemented within sound processor 302 and cochlear implant 308 (i.e., circuitry 602, 604, 606, and 608) may also be simplified and made more efficient (e.g., so as to have a smaller physical footprint, so as to be reduced in cost, etc.) when only a single carrier frequency is used for both transmission and receiving of data.

Returning to FIG. 5, forward telemetry signal 500 is shown to incorporate various components including an RF Power 502 component delivered at the carrier frequency and a self-clocking data signal 504 modulated onto RF power 502 and from which a clock signal 506 and a forward telemetry data signal 508 may be recovered or otherwise derived. Each of RF power 502 and signals 504 through 508 will now be described in more detail.

The RF power 502 incorporated within forward telemetry signal 500 may be delivered as RF power at a suitable carrier frequency (e.g., a frequency that meets regulatory compliance standards and may be relatively low in certain examples, as described above). For instance, RF power 502 may be derived directly from the RF energy of forward telemetry signal 500 at the carrier frequency. In FIG. 5, RF power 502 will be understood to be shown over a relatively short amount of time (in comparison to the time shown for forward telemetry signal 500) so that the frequency and amplitude characteristics of forward telemetry signal 500 may be more clearly understood. Specifically, as shown, RF power 502 may oscillate at a first amplitude (e.g., 100% amplitude) for a first amount of time that may be interpreted as a first digital value (e.g., a binary '1'), and then may oscillate at a second amplitude (e.g., 80% amplitude) for a second amount of time that may be interpreted as a second digital value (e.g., a binary '0'). In this way, RF power 502 is continually delivered while forward telemetry data (in the form of self-clocking data signal 504) is modulated onto RF power 502.

Self-clocking data signal 504 may be modulated onto RF power 502 as shown in the views depicted in FIG. 5 of forward telemetry signal 500 and self-clocking data signal 504, which will both be understood to be drawn over the same time scale (in contrast to RF power 502, which, as noted above, is drawn over a shorter time scale). Forward telemetry data signal 508 and clock signal 506 may both be incorporated into, and derivable from, self-clocking data signal 504 in any suitable manner. For instance, self-clocking data signal 504 may employ a Manchester encoding to represent both forward telemetry data signal 508 and clock signal 506, which, as shown, is synchronous with forward telemetry data 508. While FIG. 5 illustrates a Manchester encoding in accordance with IEEE standard 802.3, it will be understood that other Manchester standards (e.g., a Manchester standard that is inverse to the IEEE 802.3 standard such that the high levels shown in self-clocking data signal 504 would be low and the low levels would be high) may be used in certain implementations. Additionally, in still other examples, other suitable self-clocking encodings (i.e., besides Manchester encodings) may be used as may serve a particular implementation.

While forward telemetry signal 500 incorporates clock signal 506 as a clock synchronous with forward telemetry data signal 508, it will be understood, as described above, that clock signal 506 is derived or recovered from self-clocking data signal 504, rather than being modulated onto forward telemetry signal 500 directly as such. In half-duplex implementations of system 300 such as implementation 600-A of FIG. 6A, clock signal 506 may only be needed to serve as a clock for forward telemetry data 508. However, in full-duplex implementations of system 300, such as implementation 600-B of FIG. 6B, clock signal 506 may not only serve as a clock for forward telemetry data 508 but also for a backward telemetry signal that is transmitted back to sound processor 302 by cochlear implant 308 and that incorporates backward telemetry data that is synchronous with clock signal 506. For example, once clock signal 506 is recovered from forward telemetry signal 500 (i.e., from self-clocking data signal 504), clock signal 506 may serve as a clock for all data processing performed by cochlear implant 308, including the generating and transmitting of backward telemetry data. As such, any backward telemetry data generated and transmitted by cochlear implant 308 may be synchronous with clock signal 506 just as is forward telemetry data 508.

As with clock signal 506, forward telemetry data 508 will be understood, as described above, to be derivable or recoverable from self-clocking data signal 504, rather than being modulated onto forward telemetry signal 500 directly as such. Together with clock signal 506, forward telemetry data 508 may be processed by cochlear implant 308 to receive and act on any information as may be represented in forward telemetry data 508. For example, as described above, forward telemetry data 508 may include instructions sent by sound processor 302 to direct cochlear implant 308 regarding how to apply stimulation to the recipient by way of an electrode lead associated with cochlear implant 308. The data rate of forward telemetry data 508 may need to be relatively high in order for system 300 to induce the hearing sensation in the recipient in real time. For example, transmitting instructions sufficient to stimulate the cochlea for each of several frequency channels associated with the cochlea may require a data transfer rate of 1.0 Mbps or higher.

When a telemetry signal such as forward telemetry signal 500 is transmitted with modulated telemetry data at a relatively high rate, such as described above, a relatively wide bandwidth of an inductive link through which the signal is transmitted allows the signal to be transmitted with fast edges (e.g., steep rising and falling edges such as shown illustrated for signals 504 through 508 in FIG. 5). Thus, when there is sufficient bandwidth for fast edges to be represented, telemetry data may be transferred at a relatively high data rate. In contrast, however, when an inductive link has a relatively narrow bandwidth (e.g., as may be the case for narrowband link 314 for the reasons described above), various types of distortion (e.g., slower edges, wandering direct current ("DC") voltage levels, etc.) may be introduced onto telemetry signals transferred thereon. As a result, it may not be possible to recover information embedded in the signal unless the distortion is compensated for.

Figure 7:
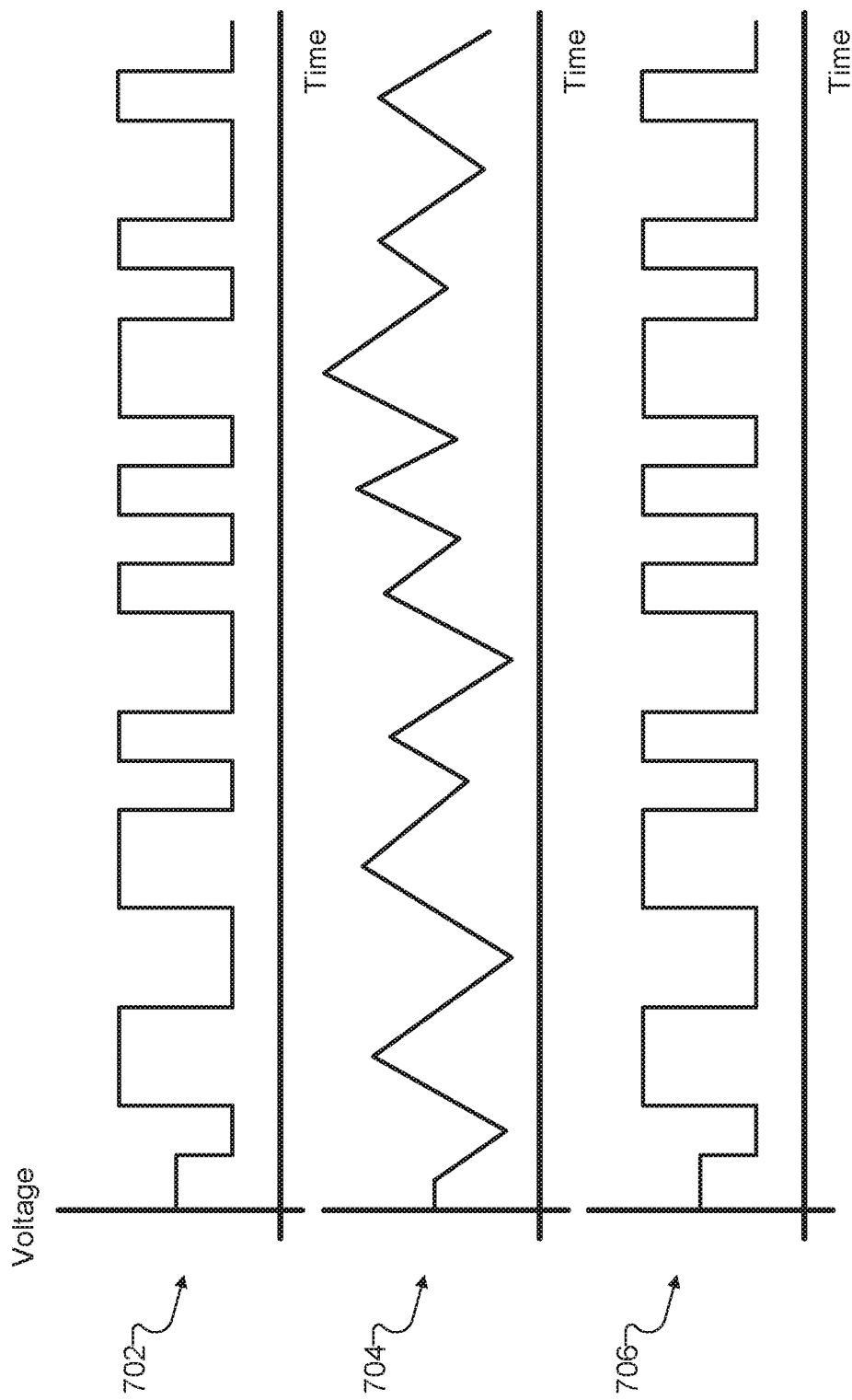
FIG. 7 illustrates exemplary distortion that may be introduced onto a forward telemetry signal as a result of bandwidth limitations imposed by a transcutaneous narrowband inductive link, and how equalization operations may compensate for such distortion according to principles described herein.

To illustrate, FIG. 7 shows exemplary distortion that may be introduced onto a telemetry signal as a result of bandwidth limitations imposed by a transcutaneous narrowband inductive link, as well as how equalization operations may compensate for such distortion according to principles described herein. Specifically, as shown, FIG. 7 depicts a telemetry data signal 702 that is similar to self-clocking data signal 504, which was described as being modulated onto forward telemetry signal 500 above, with respect to FIG. 5, Accordingly, it will be understood that telemetry data signal 702 may similarly implement a self-clocking data signal that may be modulated onto a carrier signal, and that telemetry signal 702 may incorporate both a data signal and a clock signal that can be recovered using a particular protocol (e.g., a Manchester protocol or the like). While the telemetry data signal 702 is shown in a non-modulated form (i.e., without yet being modulated onto a carrier signal), it will be understood that telemetry data signal 702, as well as other signals shown in non-modulated form in FIG. 7 that are derived therefrom, may be modulated onto a carrier signal having a carrier frequency significantly higher than the data rate of the signals shown in FIG. 7.

While telemetry data signal 702 is shown to have perfectly vertical edges (i.e., very fast edges that would require a wide bandwidth to transmit), a distorted signal 704 depicts what telemetry data signal 702 may look like when carried by a transcutaneous narrowband inductive link such as narrowband link 314. As shown, signal 704 has much slower, sloping (i.e., non-vertical) edges, significant DC wander (i.e., such that some high values are higher than others, some low values are lower than others, etc.), and is overall a very distorted version of the original representation of telemetry data signal 702. As described above, such distortions may result from bandwidth limitations imposed by the narrowness of the bandwidth of a transcutaneous narrowband inductive link. Additionally or alternatively, distortion may result from multi-path and/or other transmission fading that occurs on the inductive link. Accordingly, in order for accurate, reliable, and usable data and/or clock signals to be recovered from distorted signal 704, the distortions may be compensated for by way of equalization circuitry in any of the ways described herein.

A compensated signal 706 is also shown in FIG. 7 to depict how distorted signal 704 may be equalized to compensate for the distortions imposed by the bandwidth limitations of the transcutaneous narrowband inductive link, and to again manifest fast, vertical edges and other characteristics of the original signal 702 that was transmitted. Equalization operations that are used to derive compensated signal 706 from distorted signal 704 may allow the receiving device (e.g., cochlear implant 308 in the case of a forward telemetry signal) to properly restructure distorted signal 704 and thereby properly recover the data and/or clock signals that may be built into the original signal.

To this end, equalization operations may be performed by any suitable equalization circuitry and/or in any manner as may serve a particular implementation. For example, a single fixed zero may be sufficient for equalizing signals in certain implementations due to the limited range of the coupling coefficient, while an adaptive equalization in a digitized detection system may be employed in other implementations. Such equalization operations may be performed by analog, mixed signal, or digital signal processing in various examples.

As mentioned above, equalization circuitry may be implemented on either or both sides of a particular transcutaneous narrowband inductive link, and, as such, the equalization circuitry may be configured to perform equalization operations on a telemetry signal either prior or subsequent to transmission of that signal. Accordingly, considering a single telemetry signal (e.g., a forward telemetry signal), equalization circuitry may be implemented prior to transmission at the transmitter side (e.g., such that the distortion imposed by the transcutaneous narrowband inductive link corrects the pre-distorted signal), subsequent to being received at the receiver side (e.g., such that distortion imposed by the transcutaneous narrowband inductive link is compensated after the signal is received), or partly before and after the communication in a hybrid manner at both the transmitter and receiver sides.

Forward telemetry signals and backward telemetry signals may both be equalized at the transmitter and/or receiver ends in this way so as to best serve a particular implementation. Accordingly, in full-duplex implementations of system 300 such as implementation 600-B, all of the equalization circuitry may be implemented on the sound processor side, on the cochlear implant side, or on equalization circuitry implemented at both sides.

Figure 8:
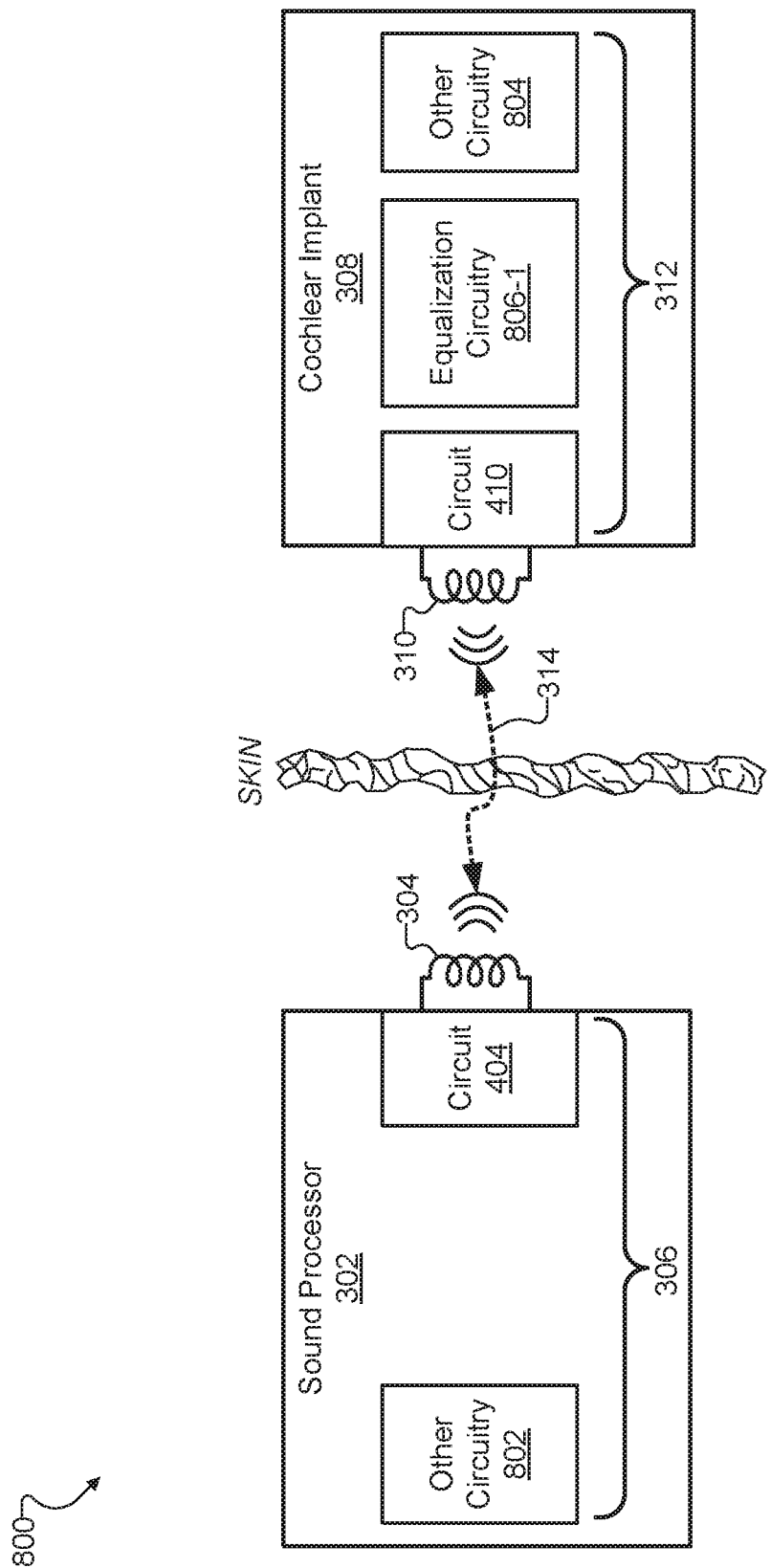
FIGS. 8-10 illustrate exemplary configurations in which equalization circuitry is implemented in different ways to thereby facilitate recovery of forward telemetry data from a forward telemetry signal according to principles described herein.
Figure 9:
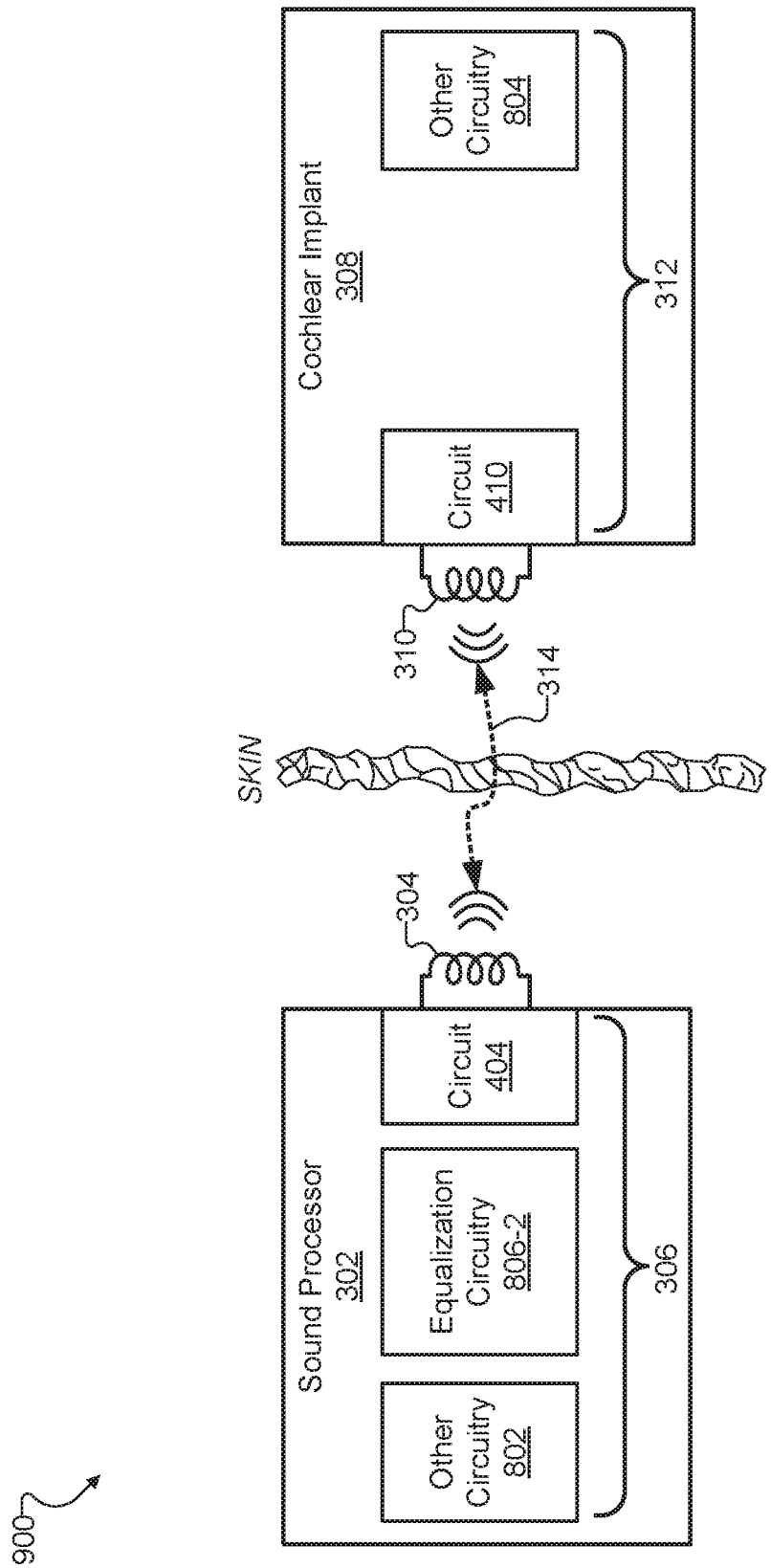
Figure 10:
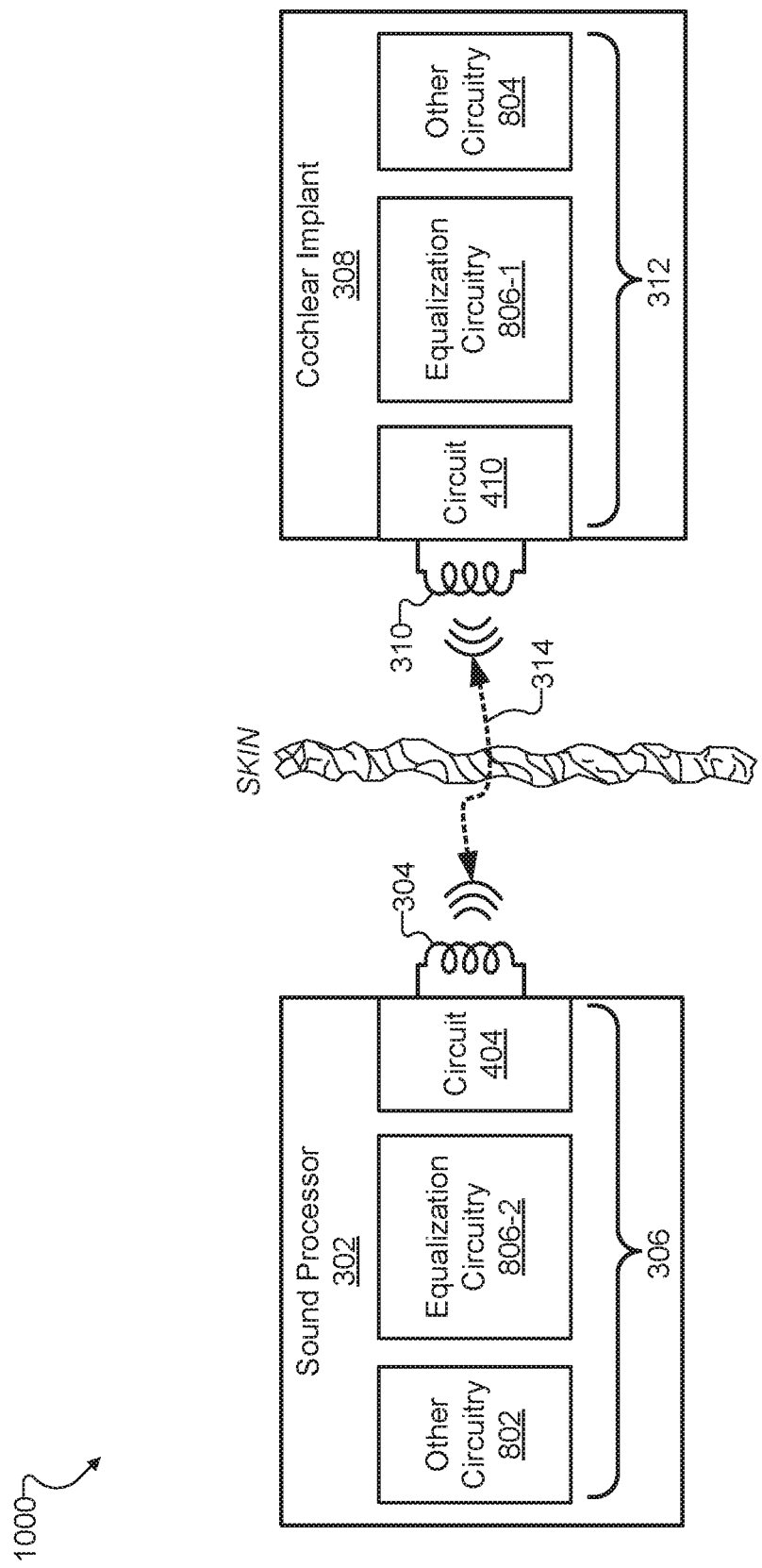

To illustrate, FIGS. 8, 9, and 10 show exemplary configurations 800, 900 and 1000, respectively, in which equalization circuitry is implemented in different ways to thereby facilitate recovery forward telemetry data (e.g., such as forward telemetry data 508) from a forward telemetry signal (e.g., such as forward telemetry signal 500). Each of configurations 800 through 1000 show the same components of system 300, including sound processor 302, sound processor coil 304, and cochlear implant 308, RF driver/receiver circuit 404, narrowband link 314, cochlear implant 308, cochlear implant coil 310, RF driver/receiver circuit 410, and so forth, Additionally, within sound processor 302, sound processor circuitry 306 is shown to include at least RF driver/receiver circuit 404 and other circuitry 802 (which will be understood to include other circuitry described above to be implemented in sound processor circuitry 306). Similarly, within cochlear implant 308, cochlear implant circuitry 312 is shown to include at least RF driver/receiver circuit 410 and other circuitry 804 (which will be understood to include other circuitry described above to be implemented in cochlear implant circuitry 312).

The difference between configurations 800, 900, and 1000, is in the manner of implementing equalization circuitry for facilitating recovery of, in this example, forward telemetry signal 500. In FIG. 8, equalization circuitry 806-1 is integrated exclusively within cochlear implant 308 (i.e., within cochlear implant circuitry 312). Accordingly, in this example, no equalization circuitry is implemented in sound processor 302 (at least not for equalizing forward telemetry signal 500) and equalization circuitry 806-1 is configured to compensate for the distortion introduced onto forward telemetry signal 500 by compensating, subsequent to receiving forward telemetry signal 500, forward telemetry signal 500 for distortion that was introduced onto the signal.

It may be desirable for equalization circuitry 806-1 to be implemented exclusively on cochlear implant 308 because doing so may allow ASK or OOK modulation techniques described herein to be employed. To the contrary, if signals are to be pre-distorted prior to transmission, other modulation techniques and/or driver technologies may be employed instead of the ASK or OOK modulation described herein, and such technologies may be associated with driver circuits that are less ideal in certain respects (e.g., more complex to design, more expensive, larger, less efficient, etc.). However, even in spite of these potential advantages, certain implementations may integrate equalization circuitry on the transmitter side for various reasons.

For example, as shown in FIG. 9, equalization circuitry 806-2 is integrated exclusively within sound processor 302 (i.e., within sound processor circuitry 306). Accordingly, in this example, no equalization circuitry is implemented in cochlear implant 308 (at least not for forward telemetry signal 500) and equalization circuitry 806-2 is configured to compensate for the distortion introduced onto forward telemetry signal 500 by compensating, prior to transmission of forward telemetry signal 500, forward telemetry signal 500 for distortion that is to be introduced onto the signal. In other words, as described above, equalization circuitry 806-2 may be configured to pre-distort forward telemetry signal 500 such that the distortions that are anticipated to be imposed by narrowband link 314 will correct the pre-distortions such that cochlear implant 308 will receive a non-distorted signal.

Configuration 1000 in FIG. 10 shows an implementation of system 300 in which equalization circuitry is integrated within both sound processor 302 and cochlear implant 308. Specifically, as shown, equalization circuitry 806-1 is integrated within cochlear implant 308 as part of cochlear implant circuitry 312 while equalization circuitry 806-2 is integrated within sound processor 302 as part of sound processor circuitry 306. In this example, system 300 may compensate for the distortion introduced onto the forward telemetry signal by both 1) compensating, prior to transmission of the forward telemetry signal, the forward telemetry signal for distortion that is to be introduced onto the forward telemetry signal; and 2) compensating, subsequent to receiving the forward telemetry signal, the forward telemetry signal for distortion that was introduced onto the forward telemetry signal. In other words, in this example, a forward telemetry signal may be partially pre-distorted by equalization circuitry 806-2 and transmitted by sound processor 302, and the pre-distortion may be partially compensated by narrowband link 314 and partially compensated by equalization circuitry 806-1 of cochlear implant 308.

Additionally or alternatively, equalization circuitry may be integrated within both sound processor 302 and cochlear implant 308 to support certain full-duplex implementations in which, for example, a forward telemetry signal is equalized at the receiver by equalization circuitry 806-1 and a backward telemetry signal is equalized at the receiver by equalization circuitry 806-2. Specifically, for instance, if a backward telemetry signal is transmitted together with a forward telemetry signal, additional equalization circuitry 806-2 integrated within sound processor 302 may be configured to facilitate recovery, by sound processor 302, of the backward telemetry data from the backward telemetry signal by compensating for distortion introduced onto the backward telemetry signal as a result of the bandwidth limitations imposed by narrowband link 314. As another example, if equalization circuitry 806-2 is used to pre-distort the forward telemetry signal to compensate for the bandwidth limitations, additional equalization circuitry 806-1 integrated within cochlear implant 308 may be configured to facilitate recovery, by sound processor 302, of the backward telemetry data from the backward telemetry signal by pre-compensating for distortion that is to be introduced onto the backward telemetry signal as a result of the bandwidth limitations imposed by narrowband link 314.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A cochlear implant system comprising:
   a sound processor configured to operate externally to a recipient of the cochlear implant system, the sound processor associated with a sound processor coil;
   a cochlear implant including a cochlear implant coil configured to form a transcutaneous narrowband inductive link with the sound processor coil when the cochlear implant is implanted within the recipient, the cochlear implant coil having a size larger than a size of the sound processor coil and enabling the cochlear implant to:
   receive, from the sound processor by way of the transcutaneous narrowband inductive link, a forward telemetry signal incorporating power for powering operations of the cochlear implant and forward telemetry data for directing the operations of the cochlear implant, and transmit, to the sound processor by way of the transcutaneous narrowband inductive link, a backward telemetry signal incorporating backward telemetry data;

equalization circuitry integrated within the cochlear implant and configured to facilitate recovery, by the cochlear implant, of the forward telemetry data from the forward telemetry signal by compensating for distortion introduced onto the forward telemetry signal as a result of bandwidth limitations imposed by the transcutaneous narrowband inductive link; and additional equalization circuitry integrated within the sound processor and configured to facilitate recovery, by the sound processor, of the backward telemetry data from the backward telemetry signal by compensating for distortion introduced onto the backward telemetry signal as a result of the bandwidth limitations imposed by the transcutaneous narrowband inductive link.

2. The cochlear implant system of claim 1, wherein:
the sound processor is implemented within a single housing; and
the sound processor coil is integrated within the single housing of the sound processor such that the transcutaneous narrowband inductive link formed between the sound processor coil and the cochlear implant coil does not employ a headpiece associated with the sound processor and housed in a separate housing from the sound processor.

3. The cochlear implant system of claim 1, wherein the forward telemetry signal and the backward telemetry signal are both transmitted on a same carrier frequency.

4. The cochlear implant system of claim 1, wherein:
the additional equalization circuitry is further configured to compensate, prior to transmission of the forward telemetry signal, the forward telemetry signal for distortion that is to be introduced onto the forward telemetry signal.

5. The cochlear implant system of claim 1, wherein the forward telemetry signal is generated using an amplitude shift keying protocol whereby the power is delivered as radio frequency (RF) power at a carrier frequency and the forward telemetry data is modulated onto the RF power by adjusting an amplitude of the RF power in a manner that represents digital values of the forward telemetry data.

6. The cochlear implant system of claim 1, wherein the power incorporated within the forward telemetry signal is delivered as radio frequency (RF) power at a carrier frequency and the forward telemetry data is modulated onto the RF power at a rate exceeding 1.0 megabits per second (mbps).

7. The cochlear implant system of claim 1, wherein:
the forward telemetry signal further incorporates a clock signal synchronous with the forward telemetry data; and
the cochlear implant coil further enables the cochlear implant to transmit, to the sound processor by way of the transcutaneous narrowband inductive link, a backward telemetry signal incorporating backward telemetry data that is synchronous with the clock signal incorporated in the forward telemetry signal.

8. The cochlear implant system of claim 1, wherein:
the forward telemetry data is incorporated in a self-clocking data signal modulated onto the power of the forward telemetry signal; and
the self-clocking data signal employs a Manchester encoding to represent both the forward telemetry data and a clock signal synchronous with the forward telemetry data.

* * * * *